(12) United States Patent
Peijster (10) Patent No.: US 9,939,728 B2
(45) Date of Patent: Apr. 10, 2018

(54) VACUUM CHAMBER WITH A THICK ALUMINUM BASE PLATE

(75) Inventor: Jerry Johannes Martinus Peijster, Houten (NL)

(73) Assignee: MAPPER LITHOGRAPHY IP B.V., Delft (NL)

( * ) Notice: Subject to any disclaimer, the term of this patent is extended or adjusted under 35 U.S.C. 154(b) by 447 days.

(21) Appl. No.: 14/344,067

(22) PCT Filed: Sep. 12, 2012

(86) PCT No.: PCT/EP2012/067792
§ 371 (c)(1),
(2), (4) Date: Feb. 10, 2015

(87) PCT Pub. No.: WO2013/037802
PCT Pub. Date: Mar. 21, 2013

(65) Prior Publication Data
US 2015/0144789 A1    May 28, 2015

Related U.S. Application Data

(60) Provisional application No. 61/533,681, filed on Sep. 12, 2011.

(51) Int. Cl.
*H01J 37/16* (2006.01)
*H01J 37/18* (2006.01)
(Continued)

(52) U.S. Cl.
CPC ............ *G03F 7/2014* (2013.01); *B82Y 10/00* (2013.01); *B82Y 40/00* (2013.01); *G01N 21/88* (2013.01);
(Continued)

(58) Field of Classification Search
CPC .......... H01J 37/16; H01J 37/20; H01J 37/261; H01J 37/3174
See application file for complete search history.

(56) References Cited

U.S. PATENT DOCUMENTS 3,849,647 A * 11/1974 Koike ..................... H01J 37/28
                                                        250/306
4,545,888 A * 10/1985 Walsh .................... B01D 57/02
                                                        204/613

(Continued)

FOREIGN PATENT DOCUMENTS

EP    1111473 A2    6/2001
EP    1143492 A1    10/2001
(Continued)

*Primary Examiner* — Jason McCormack
*Assistant Examiner* — Sean Luck
(74) *Attorney, Agent, or Firm* — Hoyng Rock Monegier LLP; David P. Owen (57) ABSTRACT

A target processing machine (100), such as a lithography or inspection machine, comprising a rigid base plate (150), a projection column (101) for projecting one or more optical or particle beams on to a target (130), a support frame (102) supporting the projection column, the support frame being supported by and fixed to the base plate, a stage comprising a movable part (128) for carrying the target and a fixed part (132, 133) being supported by and fixed to the base plate, a beam sensor (160) for detecting one or more of the beams projected by the column, the beam sensor at least in part being supported by and fixed to the base plate, and a vacuum chamber (110) enclosing the support frame and the column, for maintaining a vacuum environment in the interior space of the chamber, the vacuum chamber formed with the base plate forming part thereof, and supporting a plurality of wall panels (171, 172) including a plurality of side wall panels (171) supported by and fixed thereto.

19 Claims, 6 Drawing Sheets

(51) Int. Cl.
  *H01J 37/24*   (2006.01)
  *G03F 7/20*    (2006.01)
  *H01L 21/67*   (2006.01)
  *H01J 37/317*  (2006.01)
  *B82Y 10/00*   (2011.01)
  *B82Y 40/00*   (2011.01)
  *G01N 21/88*   (2006.01)
  *H01J 37/20*   (2006.01)
  *H01J 37/26*   (2006.01)

(52) U.S. Cl.
  CPC ........ *G03F 7/7085* (2013.01); *G03F 7/70841* (2013.01); *H01J 37/16* (2013.01); *H01J 37/18* (2013.01); *H01J 37/20* (2013.01); *H01J 37/24* (2013.01); *H01J 37/261* (2013.01); *H01J 37/3174* (2013.01); *H01J 37/3177* (2013.01); *H01L 21/6719* (2013.01); *G01N 2201/022* (2013.01); *H01J 2237/28* (2013.01)

(56) References Cited

U.S. PATENT DOCUMENTS

| | | | |
|---|---|---|---|
| 4,687,936 A | 8/1987 | McIntyre et al. | |
| 4,733,954 A * | 3/1988 | Reinheimer | G02B 21/24 359/385 |
| 4,805,000 A | 2/1989 | Ogawa et al. | |
| 5,117,997 A * | 6/1992 | Fink | A61B 50/36 206/510 |
| 5,528,118 A * | 6/1996 | Lee | G03F 7/70716 318/38 |
| 6,031,598 A | 2/2000 | Tichenor et al. | |
| 6,147,745 A * | 11/2000 | Kim | G03F 7/70225 355/53 |
| 6,879,375 B1 | 4/2005 | Kayama | |
| 6,930,756 B2 | 8/2005 | Akutsu et al. | |
| 6,940,582 B1 | 9/2005 | Tanaka | |
| 6,999,162 B1 | 2/2006 | Takahashi | |
| 7,460,208 B2 | 12/2008 | Bleeker et al. | |
| 7,540,656 B1 * | 6/2009 | Stochl | G01N 25/18 374/29 |
| 7,576,831 B2 | 8/2009 | Van Groos et al. | |
| 2002/0048003 A1 | 4/2002 | Haney et al. | |
| 2002/0061245 A1 | 5/2002 | Hasegawa et al. | |
| 2002/0109090 A1 * | 8/2002 | Nakasuji | B82Y 10/00 250/311 |
| 2003/0196760 A1 * | 10/2003 | Tyler | H01J 37/32082 156/345.47 |
| 2004/0017167 A1 * | 1/2004 | Nishi | F16F 15/0275 318/114 |
| 2004/0083966 A1 * | 5/2004 | Takahashi | G03F 7/70833 118/715 |
| 2004/0095548 A1 | 5/2004 | Lim et al. | |
| 2004/0113101 A1 | 6/2004 | Li et al. | |
| 2004/0137384 A1 | 7/2004 | Hara et al. | |
| 2004/0149881 A1 | 8/2004 | Allen | |
| 2005/0168076 A1 * | 8/2005 | Hazelton | G03F 7/70716 310/12.04 |
| 2006/0054278 A1 * | 3/2006 | Makino | H01J 37/32522 156/345.27 |
| 2006/0164093 A1 * | 7/2006 | Ooe | C02F 1/4606 324/432 |
| 2006/0187428 A1 | 8/2006 | Bleeker et al. | |
| 2008/0247845 A1 | 10/2008 | Mochizuki et al. | |
| 2009/0059190 A1 | 3/2009 | Tanaka et al. | |
| 2009/0086178 A1 * | 4/2009 | Shibazaki | G03F 7/70883 355/53 |
| 2009/0168036 A1 | 7/2009 | Hara et al. | |
| 2010/0002220 A1 | 1/2010 | Tanaka | |
| 2010/0124610 A1 * | 5/2010 | Aikawa | C23C 16/4584 427/255.28 |
| 2010/0157276 A1 | 6/2010 | Shibazaki | |
| 2010/0171022 A1 * | 7/2010 | Fujimaki | G03F 7/70833 248/559 |
| 2010/0263192 A1 | 10/2010 | Phillips | |
| 2010/0270299 A1 * | 10/2010 | Baltussen | H01J 37/16 220/4.33 |
| 2011/0042579 A1 | 2/2011 | De Boer et al. | |
| 2012/0069317 A1 | 3/2012 | Peijster | |
| 2012/0208360 A1 | 8/2012 | Tanaka et al. | |

FOREIGN PATENT DOCUMENTS

| | | | |
|---|---|---|---|
| JP | 2000 357646 A | 12/2000 | |
| JP | 2006 261212 A | 9/2006 | |
| JP | 2008 129358 A | 6/2008 | |
| NL | EP 1111473 A2 * | 6/2001 | G03F 9/7049 |
| WO | WO 00 41875 A1 | 7/2000 | |
| WO | WO 2010 094724 A1 | 8/2010 | |

\* cited by examiner

VACUUM CHAMBER WITH A THICK ALUMINUM BASE PLATE

BACKGROUND OF THE INVENTION

Field of the Invention

The invention relates to a vacuum chamber for a lithographic apparatus having an integrated base plate.

BRIEF SUMMARY OF THE INVENTION

A target processing machine, such as a lithography or inspection machine, comprising a rigid base plate, a projection column for projecting one or more optical or particle beams on to a target, a support frame supporting the projection column, the support frame being supported by and fixed to the base plate, a stage comprising a movable part for carrying the target and a fixed part being supported by and fixed to the base plate, a beam sensor for detecting one or more of the beams projected by the column, the beam sensor at least in part being supported by and fixed to the base plate, and a vacuum chamber enclosing the support frame and the column, for maintaining a vacuum environment in the interior space of the chamber, the vacuum chamber formed with the base plate forming part thereof, and supporting a plurality of wall panels including a plurality of side wall panels supported by and fixed thereto.

The beam sensor is preferably accommodated at least partially below the stage, and the base plate preferably includes a recess or hole into which the beam sensor extends. The stage preferably comprises one or more drives for moving a movable part of the stage, the drives being located at least partially outside the vacuum chamber, and the base plate preferably includes one or more openings through which the one or more drives communicate with the movable part of the stage.

The machine preferably comprises one or more vibration isolation members between the side walls and the base plate, and the base plate preferably includes three support points on its underside for supporting the machine on a pedestal. The support frame preferably forms part of a vibration isolation module, the module comprising an intermediate body connected to the support frame by means of at least one spring element, and a support body for accommodating the projection column, the support body being connected to the intermediate body by means of at least one pendulum rod.

The wall panels are preferably assembled to form the chamber using a plurality of connection members, the connection members being adapted to removably connect the wall panels with one or more sealing members provided at the edges of the wall panels. The connection members may be adapted to locate the wall panels while providing for a small predetermined range of movement of a wall panel. The connection members may comprise pins or bolts, and the one or more of the sealing members may comprise an O-ring or C-ring disposed between adjacent wall panels. At least one face of the wall panels of the chamber may be substantially covered with a mu metal.

The beam sensor is preferably fixed to the base plate so that the beam sensor has a fixed spatial relationship with the fixed part of the stage. The base plate may comprise a center section forming an interface to the support frame and a peripheral section forming an interface with the side walls of the vacuum chamber, the base plate sections being releasably connected.

The base plate may be constructed of a single thick piece of metal. The base plate may also be made in two pieces, comprising a center section forming an interface to the support frame and a peripheral section forming an interface with the side walls of the vacuum chamber. These two sections are preferably releasably connected. Preferably, the base plate is substantially constructed of aluminium.

The base plate may have a thickness substantially greater than the wall panels of the vacuum chamber. Preferably, the base plate has sufficient mass to limit the effect of vibration on the machine without requiring a fixed connection to a supporting slab.

DESCRIPTION OF ILLUSTRATIVE EMBODIMENTS

The following is a description of various embodiments of the invention, given by way of example only and with reference to the figures. The figures are not drawn to scale and are merely intended for illustrative purposes. The invention is described in relation to a charged particle lithography system, although it may also be applied for an optical lithography system, an inspection system, and the like.

Figure 1:
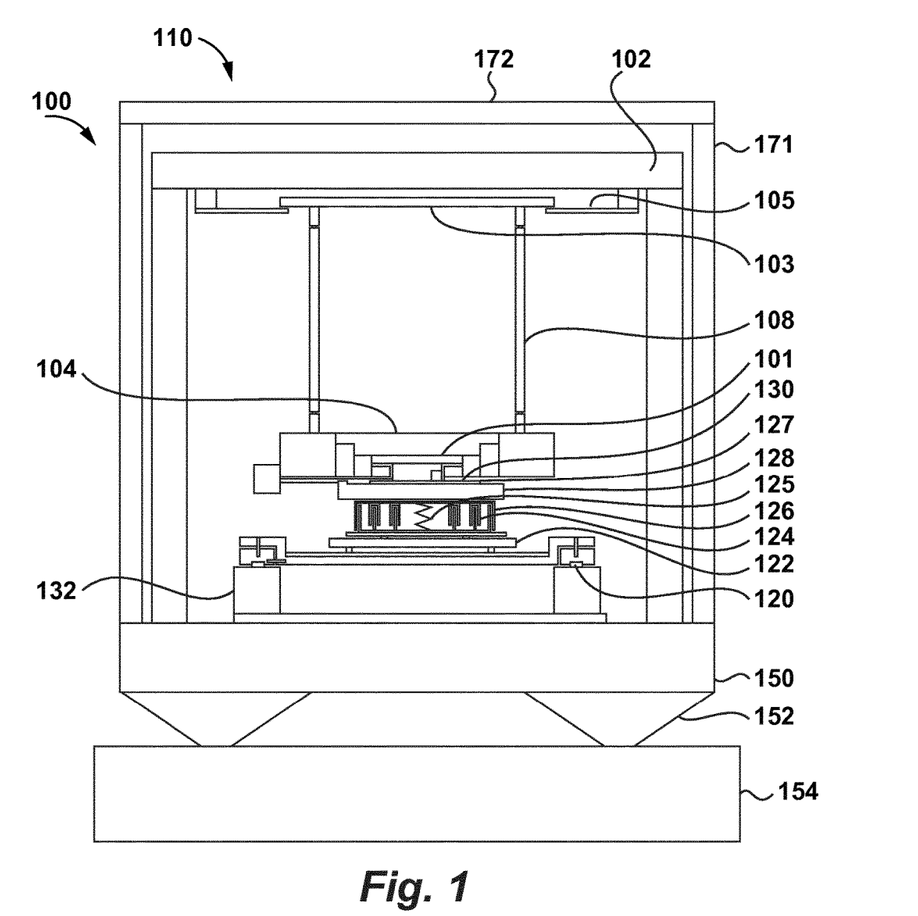

FIG. 1 schematically shows an embodiment of a target processing machine 100, such as a lithography or inspection machine. The machine comprises a projection column 101 for projecting one or more optical or particle beams on to a target, for example an electron-optical column of a multi-beamlet charged particle lithography or inspection system as schematically depicted in FIG. 1. The projection column 101 is supported by a support frame 102 located inside a vacuum chamber 110, and supported on a base plate 150.

The machine operates in a vacuum environment. A vacuum of at least $10^{-3}$ mbar is typically required for a charged particle lithography machine. All of the major elements of the machine are preferably housed in a common vacuum chamber, including for a charged particle lithography machine, the charged particle source, beamlet apertures and blanking system, projector system for projecting the beamlets onto the wafer, and the moveable wafer stage. In another embodiment the charged particle source may be housed in a separate vacuum chamber.

The target processing machine is sensitive to vibration, and in the illustrated embodiment the support frame 102 provides vibration isolation for the projection column 101. To this end, the support frame 102 comprises an intermediate body 103 and a support body 104 arranged for accommodating the projection column 101. The support frame 102 is connected to the intermediate body 103 by means of spring elements 105 comprising leaf springs in this embodiment. The spring element may also include damping elements to enable vibrational damping, particularly in the z-direction.

The support body 104 is also connected to the intermediate body 103, by means of at least one rod-like structure, further referred to as pendulum rod 108. The at least one pendulum rod 108 should be sufficiently strong to carry the body 104, which may have a mass of several hundreds of kilograms, and capable of permitting the body 104 to swing. The intermediate body 103 and/or the support body 104 may be provided with damping elements to dampen vibrations in the horizontal plane and preferably also to dampen vibrations in a rotational direction about the z-direction axis, i.e. Rz. The pendulum rods 108 comprise two flexure points, which may be created by locally reducing the cross-sectional area of the rod 108 at the point of flexure. The presence of the two flexure points causes the swinging motion of the support body 104 to occur in the horizontal plane, i.e. the xy-plane. The term "flexure point" used herein is meant to refer to a point about which a part of the rod 108 at one side of the flexure point is able to pivot and/or swivel with respect to a part of the rod 108 at the other side of the flexure point.

The target 130, such as a substrate or wafer, is held on a substrate support structure 127, which is arranged on a movable stage. The stage comprises a movable part, chuck 128, for carrying the target and a fixed part 132, 133 being supported by and fixed to the base plate. The stage further comprises a long-stroke section including an X-stage 120 arranged for movement in the x-direction (in FIG. 1 in the direction into and out of the paper) and a Y-stage 122 arranged for movement in the y-direction (in FIG. 1 in a horizontal direction). The stage short-stroke section comprises positioners 124 for moving the chuck 128 in the X, Y, and/or Z-direction and in one or more rotational directions Rz, Rx, Ry. The positioners typically take the form of electro-motors, preferably linear motors, preferably comprising Lorentz-type actuators. A gravity compensation spring 125 for decoupling vibrations in the support frame 102 from the substrate support structure 127 and the target 130 provided thereon.

Figure 2:
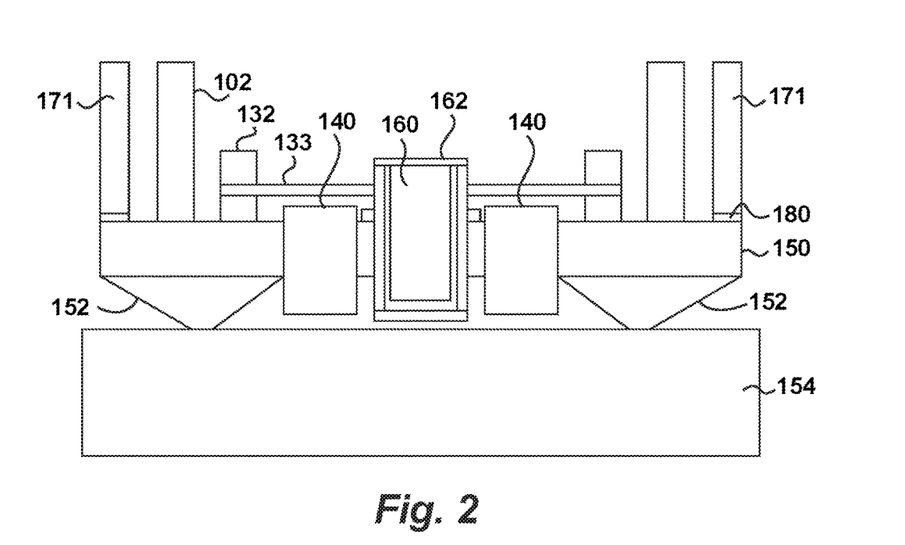

FIG. 2 shows a horizontal cross-sectional view through the base plate 150. The base plate 150 is preferably made from a thick and rigid block of metal such as aluminium. The support frame 102 is supported by and fixed to the upper side of the base plate, and the fixed part 132, 133 of the stage is also supported by and fixed to the base plate. The base plate includes supporting legs 152 for supporting the machine on a pedestal 154. The base plate preferably has three supporting legs to provide stable support for the machine on the pedestal. The legs are preferably formed as an integral part of the base plate, the metal base plate being machined in one process to form the legs and interfaces to other components in one process from a block of metal so that a single error and high accuracy is defined. The legs preferably take the form of inverted pyramids with three or more sides and a flattened portion at the peak of the pyramid where each leg rests on the pedestal.

The base plate 150 includes interfaces for the beam sensor 160, the fixed part of the stage 132, 133, the support frame 102, and the vacuum chamber walls 171. The interfaces are formed on the top side of the base plate.

The base plate 150 may include one or more openings through which one or more drives 140 are arranged. The drives are preferably located at least partially outside the vacuum chamber. Although not depicted in FIG. 2, the drives are preferably physically connected with the stage for moving the movable part of the stage. A more detailed embodiment is described with reference to FIG. 7.

A beam sensor 160 is located under the stage for detecting one or more of the beams projected by the projection column. The beam sensor may be used to detect beam position, beam spot size, and other characteristics of the beams projected by the column. The beam sensor is supported by and fixed to the base plate. The beam sensor extends into a recess in the base plate, and in the embodiment of FIG. 2 the beam sensor 160 is fitted into a housing 162 which extends into a hole formed in the base plate. For measurement of beam position, it is important for the beam sensor to be located in a fixed spatial relation to the fixed part of the stage, so that measurement of beam position with respect to the stage can be made with high accuracy.

The support frame 102 is also supported by the base plate 150. In the embodiment shown in FIG. 2 the bottom of the legs of the support frame are fixed to the base plate, e.g. bolted or welded to the base plate to provide a rigid and stable support for the frame.

The vacuum chamber 110 encloses the support frame and the projection column, for maintaining a vacuum environment in the interior space of the chamber. The base plate 150 forms a part of the vacuum chamber, together with the side wall panels 171 and top wall panel 172. The side wall panels 171 which are supported by and fixed to the base plate.

Figure 3:
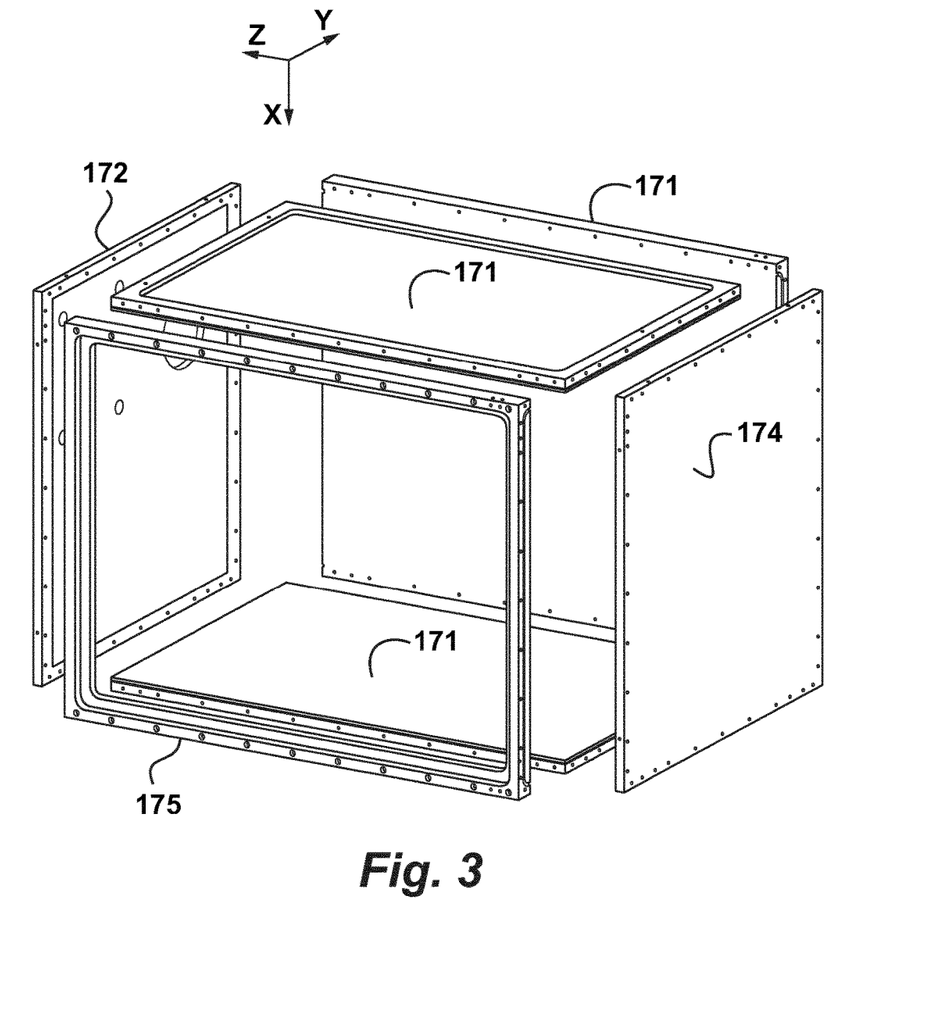

FIG. 3 shows an embodiment of the vacuum chamber having side wall panels 171, top panel 172, and temporary floor panel 174. The vacuum chamber is shown on its side as it may be positioned during assembly. The chamber may be assembled with a temporary floor panel as shown or may be assembled directly onto the base plate 150. The wall panels are joined at their edges by connection members such as bolts, enabling easy assembly and disassembly. The edges of the wall panels include a recess for locating a sealing member such as an O-ring or C-ring of the like between adjacent panels. A door frame 175 is provided for one wall, the door 176 being substantially the same size as a wall panel and in the fitting into the door frame. This provides a large opening substantially the size of an entire wall of the vacuum chamber. The top or ceiling panel 172 has holes for passage of data communication cables, electrical supply cables, cooling water tubes and the like into the chamber to connect to the machine inside the chamber.

Figure 4:
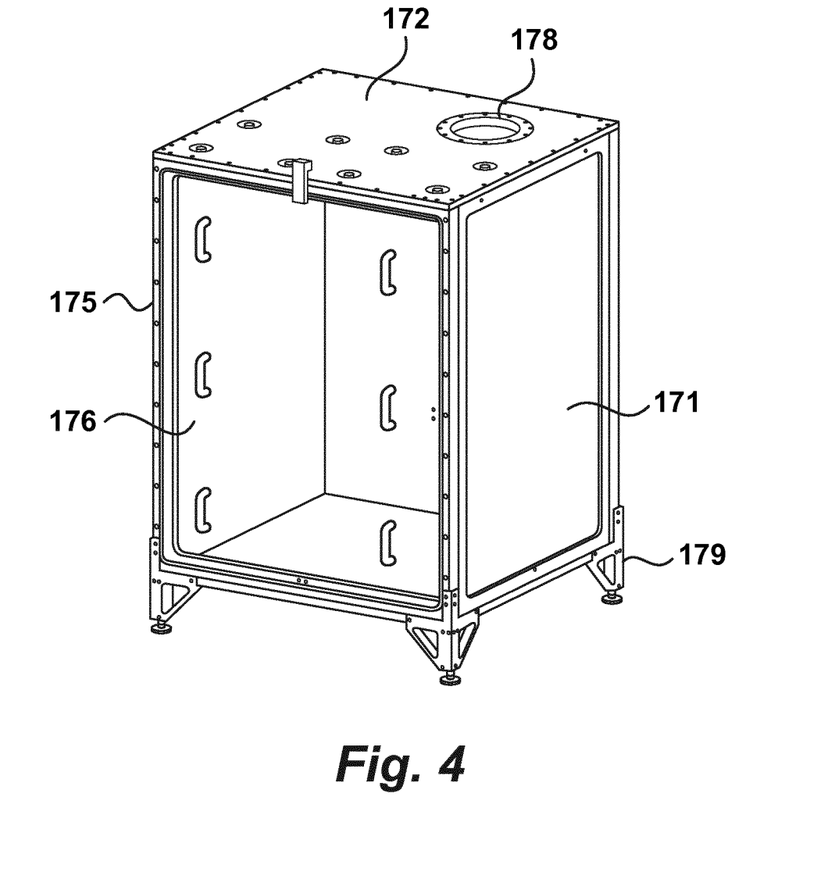

FIG. 4 shows the vacuum chamber assembled and positioned upright, sitting on temporary legs 179 used to facilitate assembly.

The vacuum chamber can be constructed as a kitset that can be shipped in a disassembled flat pack configuration and assembled on site or at a location nearer its final location. The components of the vacuum chamber may be assembled without welding, and the chamber constructed so that when the chamber is pumped down, the force of the vacuum within the chamber assists in forming a vacuum-tight construction by exerting force that acts to close any gaps between wall panels and hold the panels tightly together.

This type of construction has numerous advantages over conventional designs. The parts of the vacuum chamber may be designed as standardized components and manufactured in larger manufacturing runs, may be manufactured in parallel, and/or the manufacturing may be outsourced to specialist manufacturers to reduce lead-times and cost. Final assembly of the components may be performed without customized tooling or heavy machinery, reducing the amount of welding required and simplifying the manufacturing processes and reducing manufacturing time. The modular design provides greater flexibility in shipping the chamber, as the chamber may be shipped disassembled to reduce shipping volume and allow for separate shipment of different components. The modular design also provides greater flexibility in altering the specifications of the vacuum chamber, e.g. the size and shape of the chamber, even after shipment of the chamber from the factory.

Note that as used herein, "vacuum" does not refer to a perfect vacuum, but to an internal pressure in the interior space of the vacuum chamber that is lower than the pressure in the environment surrounding the chamber. For example, a vacuum of at least $10^{-3}$ mbar is preferred for a charged particle lithography machine, preferably $10^{-6}$ mbar.

Figure 5:
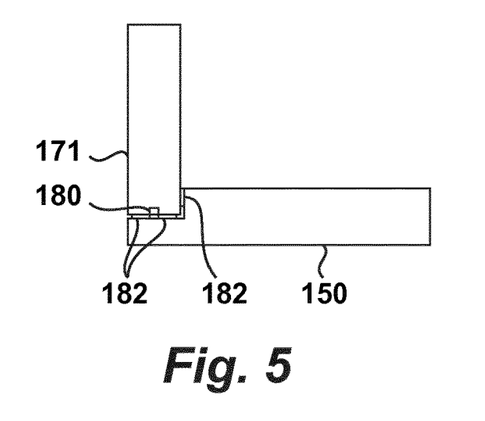

FIG. 5 is a cross sectional view showing detail of a connection between the vacuum chamber walls 171 and the base plate 150 in one embodiment. The base plate has a recessed section for receiving the bottom edge of the wall panel 171. A vacuum seal 180 is provided at the interface between the wall panel and the base plate. This may take the form of an O-ring, C-ring, or other sealing member sandwiched between the wall panel and base plate. Vibration isolation members 182 such as Viton strips may also be placed between the wall panels and the base plate to reduce transmission of vibrations between the two components. The recess may accommodate openings for passing bolts, screws or other fastening members vertically into the end faces of the walls from below the base plate, the bolts passing between the position of the vacuum seal and the outer face of the wall panels.

Figure 6:
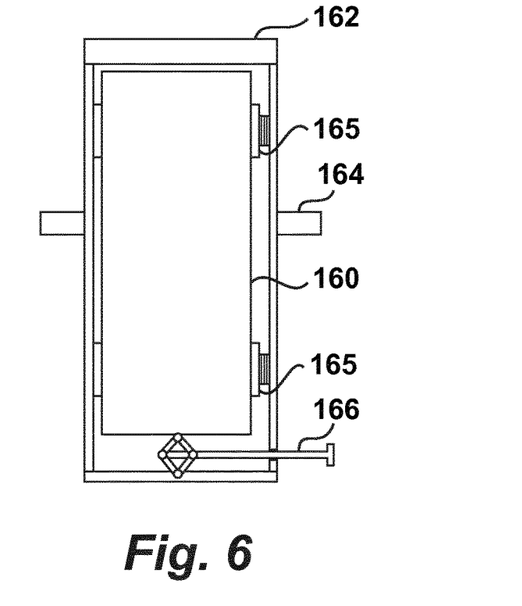

FIG. 6 is a cross sectional view showing detail of the mounting of the beam sensor 160 in one embodiment. The beam sensor is placed inside a housing 162 with an opening in the top or a transparent upper section for sensing the beams striking the sensor from above. The housing is attached to the base plate 150 via flange supports 164, and the sensor is positioned in the housing by slide supports 165 which permit vertical adjustment of the beam sensor using sensor height adjustment 166.

Figure 7:
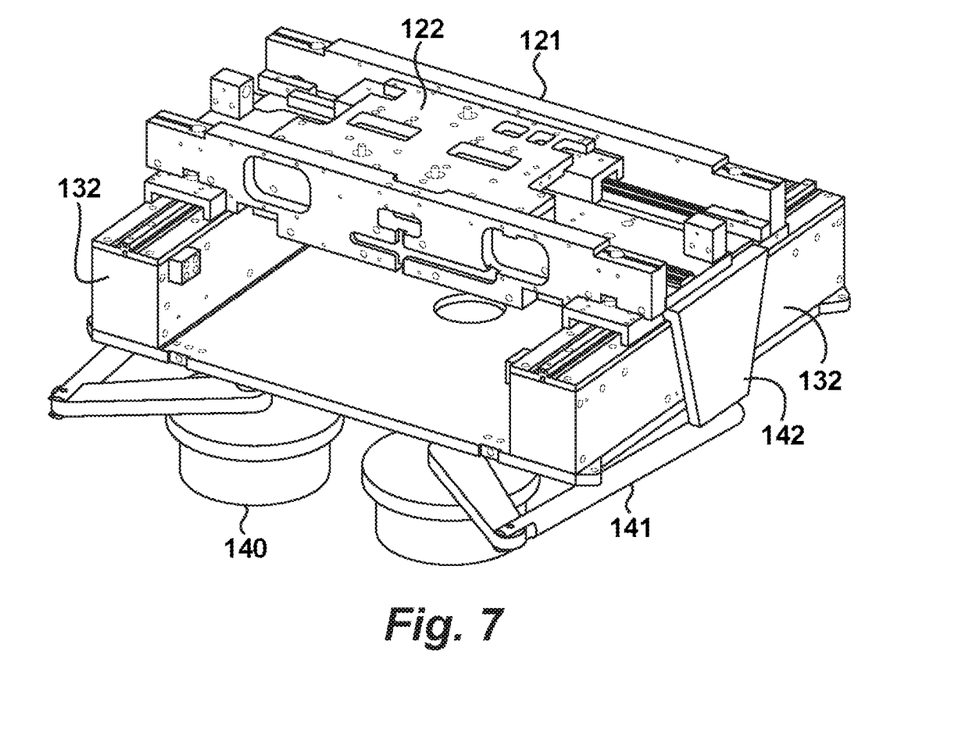

FIG. 7 shows an embodiment of a stage showing the drive motors 140 for the X-stage, with arms 141 and 142 for moving the bridge 121 on which the Y-stage 122 moves. The drive motors 140 extend under the stage and into recesses in the base plate. The fixed parts of the stage 132 are supported by the fixed to the base plate 150.

The base plate may be constructed of a single thick piece of metal, preferably aluminium, in contrast to previous designs using a relatively thin and light-weight metal base fixed to a thick stone or granite slab. In this previous design, the desired rigidity and stability was provided by the very heavy granite slab, and the metal base was attached rigidly to the slab using a relatively large number of legs fixed to the slab using bolts and set in place using a resin. In the present design, the metal base plate 150 is sufficiently thick, e.g. preferably of 25-30 cm and preferably thicker than the wall panels of the vacuum chamber, to have sufficient mass to provide the required rigidity and stability and limit the effect of vibrations, without the need for an additional thick massive slab and without the need for elaborate fixed and rigid connection between the base plate and the slab.

The present design eliminates the need for the additional slab, resulting in a simpler design with fewer critical parts and reducing the tolerance train in the lower part of the machine. The beam sensor and the target positioning system can be implemented more simply and economically and their performance improved if their relative positioning can be more accurately controlled. Limiting the number of independent elements of the base of the machine can reduce the magnitude of error by limiting the number of tolerances (otherwise the tolerances are added to one another) inherent in the manufacture and use of each part of the system. A metal base plate also has the advantage that it can be more easily and more accurately machined to precise shapes to interface accurately with other elements of the machine.

In an alternative embodiment, the base plate may be made in two pieces, comprising a center section forming an interface to the support frame and stage and a peripheral section forming an interface with the side walls of the vacuum chamber. The base plate sections made be bolted together, permitting subsequent disassembly if necessary.

The invention has been described by reference to certain embodiments discussed above. It will be recognized that these embodiments are susceptible to various modifications and alternative forms well known to those of skill in the art without departing from the spirit and scope of the invention. Accordingly, although specific embodiments have been described, these are examples only and are not limiting upon the scope of the invention, which is defined in the accompanying claims.

The invention claimed is:

1. A target processing machine, such as a lithography or inspection machine, comprising:
   a rigid base plate consisting essentially of a single thick piece of aluminum;
   a projection column for projecting one or more optical or particle beams onto a target;
   a support frame comprising a vibration isolation module for supporting the projection column, the support frame being supported by and fixed to the base plate;
   a stage comprising a movable part for carrying the target and a fixed part being supported by and fixed to the base plate;
   a vacuum chamber enclosing the support frame and the column, for maintaining a vacuum environment in the interior space of the chamber, the vacuum chamber formed with the base plate forming part thereof, and comprising a plurality of wall panels including a plurality of side wall panels supported by and fixed to the base plate,
   wherein the base plate forms a bottom wall of the vacuum chamber, and has a thickness substantially greater than the other wall panels of the vacuum chamber and sufficient mass to provide sufficient rigidity and stability and limit the effect of vibrations, and
   wherein the base plate comprises support protrusions adapted for supporting the vacuum chamber directly on a pedestal, and wherein the support protrusions are formed as an integral part of the base plate.

2. The machine of claim 1, wherein the stage comprises one or more drives for moving a movable part of the stage, the drives being located at least partially outside the vacuum chamber, and wherein the base plate includes one or more openings through which the one or more drives communicate with the movable part of the stage.

3. The machine of claim 1, further comprising one or more vibration isolation members between the side walls and the base plate.

4. The machine of claim 1, wherein the base plate includes exactly three support protrusions on its underside for supporting the machine on the pedestal.

5. The machine of claim 1, wherein the support frame forms part of a vibration isolation module, the module comprising an intermediate body connected to the support frame by means of at least one spring element, and a support body for accommodating the projection column, the support body being connected to the intermediate body by means of at least one pendulum rod.

6. The machine of claim 1, wherein the wall panels are assembled to form the chamber using a plurality of connection members, the connection members being adapted to removably connect the wall panels with one or more sealing members provided at the edges of the wall panels.

7. The machine of claim 1, wherein the connection members are adapted to locate the wall panels while providing for a small predetermined range of movement of a wall panel.

8. The machine of claim 1, wherein one or more of the sealing members comprise an O-ring or C-ring disposed between adjacent wall panels.

9. The machine of claim 1, wherein at least one face of the wall panels of the chamber is substantially covered with a mu metal.

10. The machine of claim 1, wherein the side wall panels, the support frame, and the fixed part of the stage are fixed to an upper side of the base plate, and wherein the support protrusions are provided on a lower side of the base plate.

11. The machine of claim 1, wherein the base plate comprises a center section forming an interface to the support frame and a peripheral section forming an interface with the side walls of the vacuum chamber.

12. The machine of claim 1, wherein the base plate and the support protrusions are integrally made from a single block of metal.

13. The machine according to claim 1, comprising a beam sensor for detecting one or more of the beams projected by the column, the beam sensor at least in part being supported by and fixed to the base plate.

14. The machine of claim 13, wherein the beam sensor is accommodated at least partially below the stage, and wherein the base plate includes a recess or hole into which the beam sensor extends.

15. The machine of claim 13, wherein the beam sensor has a fixed spatial relationship with the fixed part of the stage.

16. The machine of claim 1, wherein the support protrusions have a laterally converging shape with a flattened end portion adapted to rest on the pedestal.

17. The machine of claim 1, wherein the base plate has a thickness in a range of 25 centimeters to 30 centimeters, inclusive.

18. A target processing machine, such as a lithography or inspection machine, comprising:
   a rigid base plate;
   a projection column for projecting one or more optical or particle beams on to a target;
   a support frame supporting the projection column, the support frame being supported by and fixed to the base plate;
   a stage comprising a movable part for carrying the target and a fixed part being supported by and fixed to the base plate;
   a beam sensor for detecting one or more of the beams projected by the column, the beam sensor at least in part being supported by and fixed to the base plate, and
   a vacuum chamber enclosing the support frame and the column, for maintaining a vacuum environment in the interior space of the chamber, the vacuum chamber formed with the base plate forming part thereof, and comprising a plurality of wall panels including a plurality of side wall panels supported by and fixed to the base plate,
   wherein the beam sensor is accommodated at least partially below the stage, and wherein the beam sensor is placed inside a housing with an opening in the top or a transparent upper section adapted for sensing beams striking the sensor from above, the housing being attached to the base plate.

19. A vacuum chamber for a lithography or inspection machine which comprises projection column and a support frame having a vibration isolation module for supporting projection column, and a stage comprising a movable part and a fixed part, wherein the vacuum chamber comprises: a rigid base plate essentially consists of a single thick piece of aluminum, the support frame and the fixed part of the stage being supported by and fixed to the base plate;
   a vacuum chamber enclosing the support frame and the column, for maintaining a vacuum environment in the interior space of the chamber, the vacuum chamber formed with the base plate forming part thereof, and comprising a plurality of wall panels including a plurality of side wall panels supported by and fixed to the base plate,
   wherein the base plate forms a bottom wall of the vacuum chamber, and has a thickness substantially greater than the other wall panels of the vacuum chamber and sufficient mass to provide sufficient rigidity and stability and limit the effect of vibrations, and wherein the base plate comprises support protrusions adapted for supporting the vacuum chamber directly on a pedestal, and wherein the support protrusions are formed as integral part of the base plate.

\* \* \* \* \*